US00RE43374E

(19) United States
(12) Reissued Patent
Kronberg

(10) Patent Number: US RE43,374 E
(45) Date of Reissued Patent: May 8, 2012

(54) APPARATUS AND METHOD FOR BIOELECTRIC STIMULATION, HEALING ACCELERATION AND PAIN RELIEF

(75) Inventor: James W. Kronberg, Aiken, SC (US)

(73) Assignee: MedRelief Inc., Bethesda, MD (US)

(21) Appl. No.: 11/084,870

(22) Filed: Mar. 18, 2005

Related U.S. Patent Documents

Reissue of:
(64) Patent No.: 6,535,767
Issued: Mar. 18, 2003
Appl. No.: 09/935,007
Filed: Aug. 21, 2001

(51) Int. Cl.
*A61N 1/34* (2006.01)

(52) U.S. Cl. ..... 607/72; 607/51

(58) Field of Classification Search ..... 7/68–70, 7/74; 607/68–70, 74, 46, 50, 51, 72, 73
See application file for complete search history.

(56) References Cited

U.S. PATENT DOCUMENTS 3,294,092 A * 12/1966 Landauer ..... 607/66
3,516,413 A * 6/1970 Schaefer et al. ..... 607/70
3,589,370 A * 6/1971 McDonald ..... 607/70
3,946,745 A * 3/1976 Hsiang-Lai et al. ..... 607/74
4,026,304 A 5/1977 Levy
4,255,790 A * 3/1981 Hondeghem ..... 702/125
4,338,945 A * 7/1982 Kosugi et al. ..... 607/46
4,340,063 A * 7/1982 Maurer ..... 607/46
4,431,000 A * 2/1984 Butler et al. ..... 607/73
4,541,432 A * 9/1985 Molina-Negro et al. ..... 607/46
4,580,370 A 4/1986 Sarrell et al.
4,580,570 A * 4/1986 Sarrell et al. ..... 607/63
4,592,359 A * 6/1986 Galbraith ..... 607/57
4,600,010 A 7/1986 Dugot
4,607,639 A * 8/1986 Tanagho et al. ..... 607/40
4,612,934 A * 9/1986 Borkan ..... 607/62
4,754,759 A * 7/1988 Allocca ..... 607/46
4,784,142 A * 11/1988 Liss et al. ..... 607/47
4,846,181 A 7/1989 Miller
4,895,154 A * 1/1990 Bartelt et al. ..... 607/50
4,924,880 A 5/1990 O'Neill et al.
4,938,223 A * 7/1990 Charters et al. ..... 607/46
4,947,844 A * 8/1990 McDermott ..... 607/57
5,018,524 A * 5/1991 Gu et al. ..... 607/68
5,063,929 A * 11/1991 Bartelt et al. ..... 607/63
5,067,495 A 11/1991 Brehm
5,097,833 A * 3/1992 Campos ..... 607/68

(Continued)

OTHER PUBLICATIONS

European Search Report, mailed Nov. 23, 2009, for EP 02 76 6047, 3 pages.

(Continued)

*Primary Examiner* — Kennedy Schaetzle
(74) *Attorney, Agent, or Firm* — Seed IP Law Group PLLC

(57) ABSTRACT

An apparatus for generating an electrical signal for use in biomedical applications, including two timing blocks for generating timing intervals $T_1$-$T_7$, an interconnection block for combining these intervals into an output signal having predetermined relationships among the intervals, an output block for transmitting the output signal to a load, and, optionally, a filter for removing unwanted frequency components from the output signal and an adjustment block for selecting from among a plurality of output signals with predetermined characteristics. The output is a repeating succession of a burst of rectangular waves, an equalizing pulse (if needed) to cancel net DC, and a rest period of no signal.

76 Claims, 4 Drawing Sheets

U.S. PATENT DOCUMENTS

| | | | | | |
|---|---|---|---|---|---|
| 5,109,847 | A | * | 5/1992 | Liss et al. | 607/46 |
| 5,117,826 | A | * | 6/1992 | Bartelt et al. | 607/46 |
| 5,217,009 | A | * | 6/1993 | Kronberg | 607/51 |
| 5,350,414 | A | * | 9/1994 | Kolen | 607/62 |
| 5,413,596 | A | * | 5/1995 | Kronberg | 607/51 |
| 5,487,759 | A | * | 1/1996 | Bastyr et al. | 607/149 |
| 5,565,005 | A | | 10/1996 | Erickson et al. | |
| 5,571,149 | A | | 11/1996 | Liss et al. | |
| 5,601,608 | A | | 2/1997 | Mouchawar | |
| 5,723,001 | A | * | 3/1998 | Pilla et al. | 607/68 |
| 5,766,231 | A | | 6/1998 | Erickson et al. | |
| 5,851,223 | A | | 12/1998 | Liss et al. | |
| 5,974,342 | A | * | 10/1999 | Petrofsky | 607/50 |
| 6,011,994 | A | * | 1/2000 | Kronberg | 607/66 |
| 6,236,890 | B1 | | 5/2001 | Oldham | |
| 6,321,119 | B1 | | 11/2001 | Kronberg | |
| 6,505,079 | B1 | | 1/2003 | Foster et al. | |
| 6,535,767 | B1 | | 3/2003 | Kronberg | |

OTHER PUBLICATIONS

European Office Action, mailed Jul. 28, 2010, for EP 02 76 6047, 3 pages.

* cited by examiner

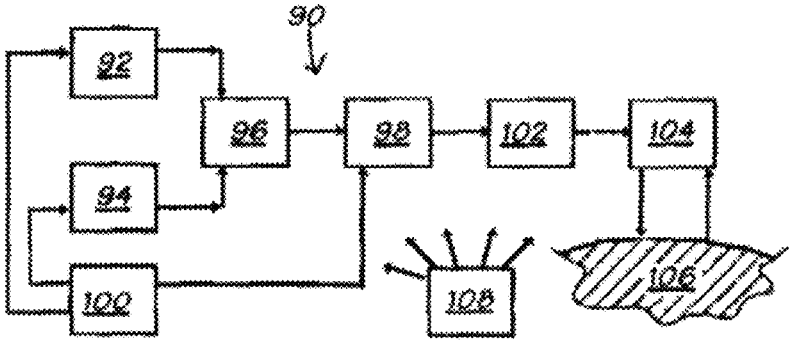
Fig. 6
(Amended)

APPARATUS AND METHOD FOR BIOELECTRIC STIMULATION, HEALING ACCELERATION AND PAIN RELIEF

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a pulsed signal generator for biomedical applications. In particular, the present invention relates to a light-weight, compact pulsed signal generator that produces an output waveform based on at least four timing intervals $T_1$-$T_4$, more preferably, a waveform based on seven timing intervals $T_1$-$T_7$.

2. Discussion of Background

Injuries, infections and degenerative conditions are major sources of pain, inconvenience, expense, lost work (and leisure) time and diminished productivity. The problems associated with these conditions grow worse with age, since an injury which would heal quickly in a young, healthy person takes much longer in one who is older, in poor health, or both. In demographically-aging societies such as now seen in most of the industrialized nations, these social and economic impacts will become increasingly magnified over the course of the next several decades.

While it is difficult to estimate the total cost of such conditions—leaving aside their impact on quality of life—the total surely amounts to many billions of dollars per year in the United States alone. For example, between five and ten million United States residents suffer broken bones every year, with many of these cases involving multiple fractures. In a young, healthy patient, many fractures need to be immobilized in a cast for six weeks or more. Even after the cast is removed, the patient's activities are frequently restricted until the healed bone regains its full strength. In the elderly, in persons with poor health or malnutrition, in patients with multiple fractures, or in patients with conditions that impact healing processes, fractures heal more slowly. In some cases, the fractures do not heal at all, resulting in the conditions known as "nonunion" or "nonunion fracture" which sometimes persists for a lifetime.

As a result, an estimated quarter-million person-years of productivity are lost in the United States due to bone fractures alone. Similar statistics can be generated not only for other classes of traumatic injury, but also for chronic conditions such as osteoarthritis, osteoporosis, diabetic and decubitus ulcers, damaged ligaments, tendonitis, and repetitive stress injuries (including the conditions commonly known as "tennis elbow" and carpal tunnel syndrome).

Since the 1960s, it has been increasingly recognized that the human body generates a host of low-level electric signals as a result of injury, stress and other factors; that these signals play a necessary part in healing and disease-recovery processes; and that such processes can be accelerated by providing artificially-generated signals which mimic the body's own in frequency, waveform and strength. Such "mimic" signals can speed the healing of skin and muscle wounds, including chronic ulcers such as those resulting from diabetes; the mending of broken bones, including most nonunion fractures; the regrowth of injured or severed nerves; and the repair of tissues damaged by repetitive motion, as in tendonitis and osteoarthritis. "Mimic" signals can also reduce swelling, inflammation, and especially pain, including chronic pain for which the usual drug-based treatments no longer bring satisfactory relief.

Some of the body's signals, such as the "injury potential" or "current of injury" measured in wounds, are DC (direct current) only, changing slowly with time. It has been found that bone fracture repair and nerve regrowth are typically faster than usual in the vicinity of a negative electrode but slower near a positive one, where in some cases tissue atrophy or necrosis may occur. For this reason, most recent research has focused on higher-frequency, more complex signals often with no net DC component.

While most complex-signal studies to date have been performed on bone fracture healing, the commonality of basic physiological processes in all tissues suggests that the appropriate signals will be effective in accelerating many other healing and disease-recovery processes. Indeed, specific frequency and waveform combinations have been observed to combat osteoarthritis and insomnia, stimulate hair growth, reduce swelling and inflammation, fight localized infection, speed the healing of injured soft tissues including skin, nerves, ligaments and tendons, and relieve pain without the substituted discomfort of TENS (transcutaneous electric nerve stimulation).

FIGS. 1A and 1B show a schematic view of a waveform 20 which has been found effective in stimulating bone fracture healing, where a line 22 (FIG. 1A) represents the waveform on a short time scale, a line 24 (FIG. 1B) represents the same waveform on a longer time scale, levels 26 and 28 represent two different characteristic values of voltage or current, and intervals 30, 32, 34 and 36 represent the timing between specific transitions. Levels 26 and 28 are selected so that, when averaged over a full cycle of the waveform, there is no net DC component. In real-world applications, waveform 20 is typically modified in that all voltages or currents decay exponentially toward some intermediate level between levels 26 and 28, with a decay time constant usually on the order of interval 34. The result is represented by a line 38 (FIG. 1C).

In a typical commercially-available device for treating fracture nonunions, interval 30 is about 200 μsec, interval 32 about 30 μsec, interval 34 about 5 msec, and interval 36 about 60 msec. Alternate repetition of intervals 30 and 32 generates pulse bursts 40, each of the length of interval 34, separated by intervals of length 36 in which the signal remains approximately at level 28. Each waveform 38 thus consists of rectangular waves alternating between levels 26 and 28 at a frequency of about 4400 Hz and a duty cycle of about 85%. The pulse bursts are repeated at a frequency of about 15 Hz and a duty cycle of about 7.5%, alternating with periods of substantially no signal. The timing of such a signal can vary broadly, since the characteristics of signals generated by bone in vivo and in vitro depend on a number of factors, including but not necessarily limited to its type, size and mineral density, and the amount of stress and its rate of application. Hence, osteoblasts are believed to be able to respond to a range of signals which differ somewhat in waveform and frequency content.

However, different tissues may respond differently to markedly different frequencies and waveforms. For example, the waveform of FIGS. 1A-C is effective in speeding the healing of a bone fracture but much less so in slowing the progress of osteoporosis. On the other hand, a waveform 50 (FIG. 2) consisting of single pulses 52 of polarity 26 lasting approximately 350-400 μsec each, alternating with intervals 54 of polarity 28 at a frequency of approximately 60-75 Hz, can slow or even reverse osteoporosis but has little effect on fracture repair. Again, the exact waveform and frequency for each application may vary.

The signal intensity may also vary; indeed, more powerful signals often give no more benefit than weaker ones, and sometimes less. This paradoxical relationship is shown schematically in FIG. 3, where a line 60 represents the magnitude of the healing effect at various signal intensities. For a typical signal (such as the signal of FIGS. 1A-C), a peak effectiveness 62 typically falls somewhere between one and ten $\mu A/cm^2$, and a crossover point 64 at about a hundred times this value. Beyond point 64, the signal may slow healing or may itself cause further injury. Similar responses are seen in other biological processes that are responsive to electrical stimulation, including cell division, protein and DNA synthesis, gene expression, and intracellular second-messenger concentrations. For example, while conventional TENS can block pain perception with a relatively strong signal, much as a jamming signal blocks radio communication, it can also lead to progressively worsening injury.

The important factors for most healing applications appears to be that the high-frequency signal appears in bursts, separated by longer intervals of quiet or no signal—i.e., the duty cycle is relatively low—and that the waveform within these bursts is itself asymmetric. Results appear to be better when frequency components above about 50 KHz are filtered out, giving transition times on the order of five μsec. Tests using sine waves, square waves, frequencies above about 50 KHz, or waveforms generally resembling that in FIG. 1 but with duty cycles approaching 50% or with excessively fast or slow rise times, have shown much lower effectiveness at otherwise-comparable power levels.

Many different types of electrical stimulation devices are available to consumers and medical professionals, producing many different waveforms ranging from constant-current or constant voltage (DC) through low-frequency to high frequency waveforms. In general, the lower-frequency waveforms and high-frequency pulses within a low-frequency envelope tend to be aimed at tissue-healing applications, while higher-frequency waveforms are used for pain relief Electrical stimulation is widely used in tissue healing applications. Here, Petrofsky (U.S. Pat. No. 5,974,342) shows a microprocessor-controlled apparatus for treating injured tissue, tendon, or muscle by applying a therapeutic current. The apparatus has several channels that provide biphasic constant voltage or current, including a 100-300 μsec positive phase, a 200-750 μsec inter-phase, and a 100-300 μsec negative phase occurring once every 12.5-25 msec.

Pilla, et al. (U.S. Pat. No. 5,723,001) disclose an apparatus for therapeutically treating human body tissue with pulsed radiofrequency electromagnetic radiation. The apparatus generates bursts of pulses having a frequency of 1-100 MHz, with 100-100,000 pulses per burst, and a burst repetition rate of 0.01-1000 Hz. The pulse envelope can be regular, irregular, or random.

Bartelt, et al. (U.S. Pat. No. 5,117,826) discloses an apparatus and method for combined nerve fiber and body tissue stimulation. The apparatus generates biphasic pulse pairs for nerve fiber stimulation, and a net DC stimulus for body tissue treatment (provided by biphasic pulse trains having a greater number of negative than positive pulses). In U.S. Pat. No. 4,895,154, Bartelt, et al. describe a device for stimulating enhanced healing of soft tissue wounds that includes a plurality of signal generators for generating output pulses. The intensity, polarity, and rate of the output pulses can be varied via a series of control knobs or switches on the front panel of the device.

Gu, et al. (U.S. Pat. No. 5,018,525) show an apparatus that generates a pulse train made up of bursts having the same width, where each burst is made up of a plurality of pulses of a specific frequency. The number of pulses varies from one burst to the next; the frequency of the pulses in each burst varies from one burst to the next corresponding to the variation in the number of pulses in each burst. The pulses have a frequency of 230-280 KHz; the duty cycle of the bursts is between 0.33% and 5.0%.

Liss, et al. (U.S. Pat. No. 5,109,847) relates to a portable, non-invasive electronic apparatus which generates a specifically contoured constant current and current-limited waveform including a carrier frequency with at least two low-frequency modulations. The carrier frequency is between 1-100,000 KHz, square-wave or rectangular-wave modulating frequencies are 0.01-199 KHz and 0.1-100 KHz. Duty cycles may vary, but are typically 50%, 50%, and 75% for the three waveforms.

Borkan's tissue stimulator (U.S. Pat. No. 4,612,934) includes an implantable, subcutaneous receiver and implantable electrodes. The receiver can be noninvasively programmed after implantation to stimulate different electrodes or change stimulation parameters (polarity and pulse parameters) in order to achieve the desired response; the programming data is transmitted in the form of a modulated signal on a carrier wave. The programmed stimulus can be modified in response to measured physiological parameters and electrode impedance.

Hondeghem (U.S. Pat. No. 4,255,790) describes a programmable pulse generating system where the time periods and sub-intervals of the output pulses are defined by signals from a fundamental clock frequency generation circuit, plus a pair of parallel sets of frequency division circuits connected to that circuit. The time periods, sub-intervals, and output waveforms are variable.

Hsiang-Lai, et al. (U.S. Pat. No. 3,946,745) provide an apparatus for generating positive and negative electric pulses for therapeutic purposes. The apparatus generates a signal consisting of successive pairs of pulses, where the pulses of each pair are of opposite polarities. The amplitude, duration, the interval between the pulses of each pair, and the interval between successive pairs of pulses are independently variable.

McDonald (U.S. Pat. No. 3,589,370) shows an electronic muscle stimulator which produces bursts of bidirectional pulses by applying unidirectional pulses to a suitable transformer.

Landauer (U.S. Pat. No. 3,294,092) discloses an apparatus that produces electrical currents for counteracting muscle atrophy, defects due to poor nutrition, removing exudates, and minimizing the formation of adhesions. The amplitude of the output signals is variable.

Kronberg (U.S. Pat. Nos. 5,217,009, 5,413,596, 6,011,994, and application Ser. No. 09/478,103 (filed Jan. 1, 2000), all incorporated herein by reference) describes signal generators for biomedical applications. The generators produce pulsed signals having fixed and variable amplitude, fixed, variable, and swept frequencies, and (in some cases) optional DC biasing.

Units designed for use in transcutaneous electroneural stimulation ("TENS") for pain relief are widely available. For example, Bastyr, et al. (U.S. Pat. No. 5,487,759) disclose a battery-powered device that can be used with different types of support devices that hold the electrode pads in position. Keyed connectors provide a binary code that is used to determine what type of support device is being used for impedance matching and carrier frequency adjustment. The carrier frequency is about 2.5-3.0 KHz, the therapeutic frequency is typically on the order of 2-100 Hz.

Kolen (U.S. Pat. No. 5,350,414) provides a device where the carrier pulse frequency, modulation pulse frequency, intensity, and frequency/amplitude modulation are controlled by a microprocessor. The device includes a pulse modulation scheme where the carrier frequency is matched to the electrode-tissue load at the treatment site to provide more efficient energy transfer.

Liss, et al. (U.S. Pat. No. 4,784,142) discloses an electronic dental analgesia apparatus and method. The apparatus generates a output with relatively high frequency (12-20 KHz) pulses with nonsymmetrical low frequency (8-20 Hz) amplitude modulation.

Bartelt, et al. (U.S. Pat. No. 5,063,929) describe a microprocessor-controlled device that generates biphasic constant-current output pulses. The stimulus intensity can be varied by the user.

Charters, et al. (U.S. Pat. No. 4,938,223) provide a device with an output signal consisting of bursts of stimuli with waxing and waning amplitudes, where the amplitude of each stimulus is a fixed percentage of the amplitude of the burst. The signal is amplitude-modulated to help prevent the adaptation response in patients.

Molina-Negro, et al. (U.S. Pat. No. 4,541,432) disclose an electric nerve stimulation device for pain relief The device produces a bipolar rectangular signal with a preselected repetition rate and width for a first time period. Then, a rectangular signal is generated at a pseudo-random rate for a second time period, and delivery of the signal is inhibited for a third, pseudo-random period of time. This protocol is said to substantially eliminate adaptation of nerve sells to the stimulation.

Butler, et al. (U.S. Pat. No. 4,431,000) show a transcutaneous nerve stimulator for treating aphasias and other neurologically-based speech and language impairments. The device uses a pseudorandom pulse generator to produce an irregular pulse train composed of trapezoidal, monophasic pulses which mimic typical physiological wave forms (such as the brain alpha rhythm). A series of such pulses has a zero DC level; a current source in the device reduces the effects of variables such as skin resistance.

Maurer (U.S. Pat. No. 4,340,063) discloses a stimulation device which can be implanted or applied to the body surface. The amplitude of the pulse decreases with a degradation in pulse width along a curve defined by a hyperbolic strength-duration curve. This is said to result in proportionately greater recruitment of nerve fibers due to the nonlinear relationship between pulse width and threshold.

The Kosugi, et al. system (U.S. Pat. No. 4,338,945) generates pulses that fluctuate in accordance with the 1/f rule. That is, the spectral density of the fluctuation varies inversely with the frequency: pleasant stimuli often have stochastic fluctuations governed by this rule. The system produces an irregular pulse train said to promote patient comfort during the stimulation.

Signal generators are also used in hearing prostheses. For example, McDermott's receiver/stimulator (U.S. Pat. No. 4,947,844) generates a series of short spaced current pulses, with between-pulse intervals of zero current having a duration longer than that of each spaced pulse. The waveform of the stimulus current includes a series of these spaced pulses of one polarity followed by an equal number of spaced pulses of opposite polarity so that the sum of electrical charge transferred through the electrodes is approximately zero.

Alloca (U.S. Pat. No. 4,754,7590 describes a neural conduction accelerator for generating a train of "staircase-shaped" pulses whose peak negative amplitude is two-thirds of the peak positive amplitude. The accelerator design is based on Fourier analysis of nerve action potentials; the output frequency can be varied between 1-1000 Hz.

Galbraith (U.S. Pat. No. 4,592,359) describes a multichannel implantable neural stimulator wherein each data channel is adapted to carry information in monopolar, bipolar, or analog form. The device includes charge balance switches designed to recover residual charge when the current sources are turned off (electrode damage and bone growth are said to be prevented by not passing DC current or charge).

Despite its great healing potential, traditional Western medicine has accepted electrotherapeutic treatment only grudgingly, and to date it is used only rarely. This seems to be a legacy from early beliefs that signals would need to have high local intensities to be effective. Most electrotherapeutic apparatus now available relies either on direct implantation of electrodes or entire electronic packages, or on inductive coupling through the skin. The need for surgery and biocompatible materials in the one case, and excessive circuit complexity and input power in the other, has kept the price of most such apparatus (apart from TENS devices) relatively high, and has also restricted its application to highly trained personnel. There remains a need for a versatile, cost-effective apparatus that can be used to provide bioelectric stimulation in a wide range of applications, including healing acceleration and pain relief

SUMMARY OF THE INVENTION

According to its major aspects and broadly stated, the present invention is an apparatus and method for generating an electrical signal for use in biomedical applications. The signal is based on at least four timing intervals $T_1$-$T_4$; more preferably, the signal is based on seven timing intervals $T_1$-$T_7$. The apparatus includes a first timing block for generating timing intervals $T_1$ and $T_2$; a second timing block for generating timing intervals $T_3$ and $T_4$ (the timing blocks also generate intervals $T_5$, $T_6$, and $T_7$ if present); an interconnection block for combining these intervals into an output signal having predetermined relationships among the intervals; an output block for transmitting the output signal to a load, a battery pack; and, optionally, a filter for removing unwanted frequency components from the output signal; and an adjustment block for selecting from among a plurality of output signals with predetermined characteristics. The signal has a first amplitude level $L_1$ during intervals $T_1$, $T_5$, and $T_6$, a second level $L_2$ during intervals $T_2$ and $T_4$, and a third level $L_3$ during interval $T_7$, where $L_3$ falls in the range between $L_1$ and $L_2$, inclusive.

The apparatus is lightweight, compact, self-contained, cost-effective to manufacture and maintain, and convenient to carry or wear for extended periods. It is safe for unsupervised home use without the need for special training, and able to generate the above-described output signal and deliver it efficiently through conductive pads making direct contact with the load. Since only low voltages and currents are used, the apparatus does not pose a shock hazard even in case of malfunction. Power is furnished by compact and inexpensive batteries, needing replacement only once in several weeks of use.

The apparatus may be used to provide electrotherapeutic treatment for human and animal patients, including but not necessarily limited to healing acceleration, relief of acute or chronic pain, and relief of swelling and/or inflammation. Since isolated cells or tissue cultures can also be affected by electrotherapeutic waveforms (appropriate electrical stimuli have been observed to modify the rates of cell metabolism, secretion, and replication), the apparatus may also be used for in vitro applications.

The output signal is an important feature of the present invention. The output signal is a waveform based on at least four timing intervals $T_1$-$T_4$ having the following relationships:

(a) $(2\times T_2)\leqq T_1\leqq(20\times T_2)$
(b) $(50\ \mu sec\leqq(T_1+T_2)\leqq 5000\ \mu sec$
(c) $T_3\geqq(10\times T_1)$
(d) $T_4\leqq 500$ msec where the signal has a first amplitude level $L_1$ during interval $T_1$ and a second amplitude level $L_2$ during intervals $T_2$ and $T_4$, where intervals $T_1$ and $T_2$ alternate through interval $T_3$, and where intervals $T_3$ and $T_4$ also alternate. Thus, intervals $T_1$ and $T_2$ are analogous to intervals 30 and 32 of FIG. 1A; intervals $T_3$ and $T_4$ are analogous to intervals 34 and 36 of FIG. 1B.

More preferably, the waveform is based on seven timing intervals $T_1$-$T_7$, with three different amplitude levels as described above. The timing intervals have, approximately, the following relationships:

(a) $(2\times T_2)\leqq T_1\leqq(20\times T_2)$
(b) $50\ \mu sec\leqq(T_1+T_2)\leqq 5000\ \mu sec$
(c) $T_3\geqq(10\times T_1)$
(d) $0\leqq T_4\leqq 500$ msec
(e) $0\leqq T_5\leqq T_1$
(f) $0\leqq T_6\leqq T_1$
(g) $0\leqq T_7\leqq 500$ msec
(h) $5\ msec\leqq(T_3+T_4+T_7)\leqq 500$ msec In a preferred embodiment, interval $T_3$ consists of the following sequence: an interval $T_5$, followed by at least one pair of intervals ($T_1$, $T_2$), and then by an interval $T_6$. The timing intervals and amplitude levels are variable, providing an output signal that can be adjusted for a wide range of therapeutic applications.

The apparatus is another important feature of the present invention. The apparatus includes timing blocks (such as oscillators or astable multivibrators) for generating the timing intervals, preferably connected so that the first timing block controls the second timing block through the interconnection block. Preferably, the apparatus includes a switching block that enables the user to select from among a plurality of paired values of intervals ($T_1$, $T_2$), and a plurality of paired values of intervals ($T_3$, $T_4$), and amplitude output levels $L_1$-$L_3$. More preferably, the transition between any two of levels $L_1$ through $L_3$ has a decay time constant no greater than approximately ½ $T_2$. Optionally, the apparatus may produce a waveform wherein all amplitude levels decay towards a value $L_4$ intermediate between $L_1$ and $L_2$ (in like manner to the signals shown in FIG. 1C). In this case, $L_4$ may or may not be equal to $L_3$, and the decay takes place with a time constant no less than approximately 10 times $T_1$. Thus, the output signal is adjustable in both waveform and amplitude to suit the needs of the individual user and the particular application.

Another feature of the present invention is the provision of interval $T_7$, during which intermediate voltage or current level $L_3$ is presented to the load rather than low level $L_2$. This feature minimizes the amount of low-frequency energy which is presented to the load (such as tissue being treated with the apparatus) during this resting interval between pulse bursts.

Still another feature of the present invention is the filter, which blocks frequencies above a selected level (i.e., frequencies greater than the highest ones intentionally generated), to create a desired transition profile or to prevent interference by external high-frequency signal sources. For example, the filter may include a shunt capacitance, a resistor network, a voltage-controlled current source, or other suitable device that simultaneously slows and controls the rate of transitions, attenuates output frequency components above about 50 KHz (or other selected frequency), and prevents interference with circuit functioning by external radio-frequency signals.

Yet another feature of the present invention is the use of dual timing blocks to generate waveforms that can be combined to produce an output waveform having selected desired characteristics. In a preferred embodiment of the invention, one of two timing blocks is controlled by the other: that is, the output of the second block is "on" or "off" depending on whether the output of the first block is "low" or "high," respectively. This results in a circuit that generates an output signal whose characteristics—frequency, duty cycle, amplitude—can be determined over a wide range by the particular selection of components. Two such circuits with output signals having appropriately-selected characteristics can be combined to produce the desired output waveform, with timing intervals $T_1$ through $T_7$, with a surprisingly simple overall circuit configuration.

Another feature of the present invention is the use of conventional, readily-available low-voltage batteries as a power source for the apparatus. This feature not only reduces the size and weight of the apparatus, but also adds to its safety and ease of use for a patient undergoing treatment. Typically, the batteries need to be replaced at infrequent intervals (generally no more than once every few weeks, depending on the output signal and the particular application), simplifying patient compliance and reducing cost. The possibility of electrical injuries is greatly reduced, since the generator is not connected to AC line current during use, does not produce high voltages, and does not generate frequencies likely to induce ventricular fibrillation. Only low power levels are required to produce therapeutic effects; thus, the generator cannot produce an electrical shock hazard even in the event of a malfunction. Thus, the invention is suitable for unsupervised home use.

Still another feature of the present invention is its versatility. The components of the apparatus are selected so as to produce an output waveform with selectable timing intervals $T_1$ through $T_7$ and output voltage (or current) levels $L_1$ through $L_3$. An apparatus with an adjustable output signal is useful for a greater variety of applications than one having a fixed output; on the other hand, medical professionals may prefer a generator having a fixed output, or an output that is adjustable only in magnitude, for outpatient use by their patients. In one embodiment of the invention, the user can select a signal for a given application by turning a dial or using a keypad to select one of a plurality of the available signals noted above.

Other features and advantages of the present invention will be apparent to those skilled in the art from a careful reading of the Detailed Description of Preferred Embodiments presented below and accompanied by the drawings.

BRIEF DESCRIPTION OF THE DRAWINGS

In the drawings,

FIG. 6 is a block diagram of an apparatus according to a preferred embodiment of the present invention;

DETAILED DESCRIPTION OF PREFERRED EMBODIMENTS

Figure 1A:
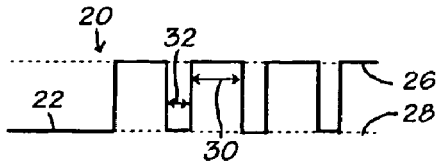
FIGS. 1A and 1B are schematic views of a waveform used in stimulating fracture healing, on a short and a long time scale, respectively.

In the following detailed description of the invention, reference numerals are used to identify structural elements, portions of elements, surfaces or areas in the drawings, as such elements, portions, surfaces or areas may be further described or explained by the entire written specification. For consistency, whenever the same numeral is used in different drawings, it indicates the same element, portion; surface or area as when first used. Unless otherwise indicated, the drawings are intended to be read together with the specification, and are to be considered a portion of the entire written description of this invention as required by 35 U.S.C. §112. As used herein, the terms "horizontal," "vertical," "left," "right," "up," "down," as well as adjectival and adverbial derivatives thereof, refer to the relative orientation of the illustrated structure as the particular drawing figure faces the reader.

The present invention is an apparatus for use in providing bioelectric stimulation in a variety of applications. The apparatus generates a waveform having approximately rectangular or quasirectangular, asymmetric pulses repeated at a chosen frequency below approximately 50 KHz, with frequencies above approximately 50 KHz filtered out. These pulses appear in bursts which themselves are repeated at a lower frequency. The characteristics of the waveform are variable to suit differing applications or target tissues to be treated, as will be described further below.

Figure 4:
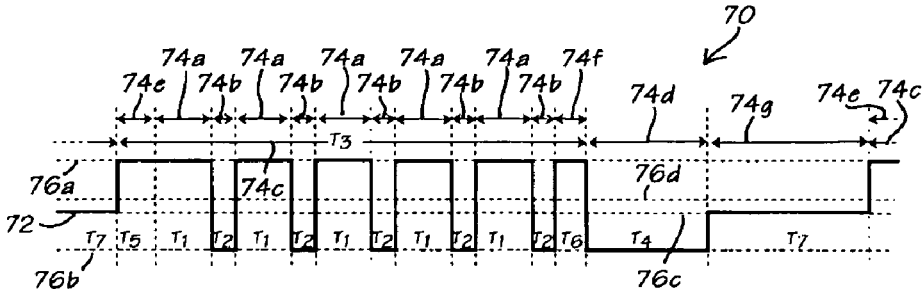
FIG. 4 illustrates a waveform according to a preferred embodiment of the present invention.

Referring now to FIG. 4, there is shown a waveform 70 according to a preferred embodiment of the present invention. Waveform 70, indicated by line 72, has seven timing intervals $T_1$-$T_7$, indicated as intervals 74a-74g, respectively, and three levels of voltage or current $L_1$-$L_3$, indicated as levels 76a-76c. While level $L_1$ is shown as being above $L_2$ in FIG. 4, it should be understood that $L_1$ is not necessarily either positive or negative with respect to $L_2$. Intervals $T_1$-$T_7$ are related as follows:

(a) $(2\times T_2)\leqq T_1\leqq(20\times T_2)$ (b) $50\ \mu sec\leqq(T_1+T_2)\leqq 5000\ \mu sec$ (c) $T_3\geqq(10\times T_1)$ (d) $0\leqq T_4\leqq 500$ msec (e) $0\leqq T_5\leqq T_1$ (f) $0\leqq T_6\leqq T_1$ (g) $0\leqq T_7\leqq 500$ msec (h) $5\ msec\leqq(T_3+T_4+T_7)\leqq 500$ msec That is, interval 74a ($T_1$) is between 2-20 times, preferably about seven times, as long as interval 74b ($T_2$), corresponding to duty cycles between about 5% and 33%. The sum of $T_1$ and $T_2$ lies in the approximate range of 50-5000 μsec. Intervals 74e ($T_5$) and 74f ($T_6$) range from zero to $T_1$ in length. Interval 74c ($T_3$) is at least approximately ten times interval 74a ($T_1$). The sum of 74c ($T_3$), 74d ($T_4$) and 74g ($T_7$) lies in the range from 5 msec to 500 msec, and is preferably about 70 msec. (It should be understood that these ranges are approximate; values of $T_1$-$T_7$ outside these ranges may also be useful.) Subject to these constraints, any one or combination of $T_4$, $T_5$, $T_6$, and $T_7$ may each have any length, including zero.

Intervals $T_1$ and $T_2$ form an alternating cycle $T_1$, $T_2$, $T_1$, $T_2$ and so forth, representing opposite phases of a rectangular wave whose frequency lies in the range from about 200 Hz-20 KHz. Similarly, intervals $T_3$, $T_4$, and $T_7$ form an alternating cycle $T_3$, $T_4$, $T_7$, $T_3$, $T_4$, $T_7$ and so forth, representing successive phases in a three-phase wave whose frequency lies between approximately 5-50 Hz. Each interval $T_3$ is subdivided into a plurality of shorter intervals beginning with a single interval $T_5$, proceeding through a plurality of intervals $T_1$ and $T_2$ alternating as described above, and ending with a single interval $T_6$ whose end coincides with that of interval $T_3$, so that a representative (if atypically short) example might be $T_5$, $T_1$, $T_2$, $T_1$, $T_2$, $T_6$. Intervals $T_4$ and $T_7$, in contrast, are not so subdivided.

First and second levels $L_1$ (level 76a) and $L_2$ (level 76b) of voltage or current are opposite in polarity and define a range between them which, within tissue undergoing treatment with waveform 70, typically spans a few mV/cm (voltage) or a few $\mu A/cm^2$ (current). Within this range lie a third and optionally a fourth voltage or current level $L_3$ (level [76] *76c*) and $L_4$ (level [76e] *76d*), either of which may have any value within the range $L_1$-$L_2$ (for many applications, both $L_3$ and $L_4$ may be zero).

During a complete cycle of waveform 70, the voltage or current assumes level $L_1$ (i.e., level 76a) during intervals $T_1$, $T_5$ and $T_6$, level $L_2$ (76b) during intervals $T_2$ and $T_4$, and level $L_3$ (76c) during interval $T_7$. (Interval $T_3$ is subdivided as previously stated.) A transition between voltage or current levels preferably approximates an exponential decay toward the new level with a time constant $\tau_1$ less than one-sixth of $T_2$. More preferably, this time constant is about 5 μsec so that frequency components above about 50 KHz are suppressed. Where convenient, the voltage or current after each such transition may also decay exponentially toward $L_4$, provided that such decay has a time constant $\tau_2$ greater than ten times $T_1$.

The decay time constant t is defined as the period during which the difference between the indicated quantity and its final value drops by a factor of e, or approximately 2.71828. After a time equal to one time constant, therefore, the difference has dropped to about 27% of what it was at the start. After three time constants, the difference is down to about 5%, and the decay may be considered substantially complete. For a transition between voltage or current levels, this decay preferably takes place in about 15 μsec or one-half of $T_2$, whichever is shorter.

Figure 1B:
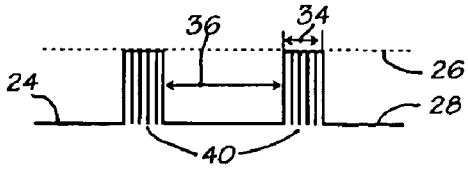
Figure 1C:
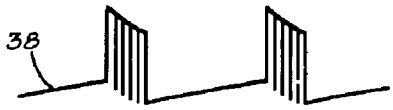
FIG. 1C shows a modified form of the waveform of FIG. 1B.
Figure 2:
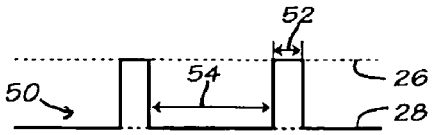
FIG. 2 shows a waveform used in the treatment of osteoporosis.
Figure 3:
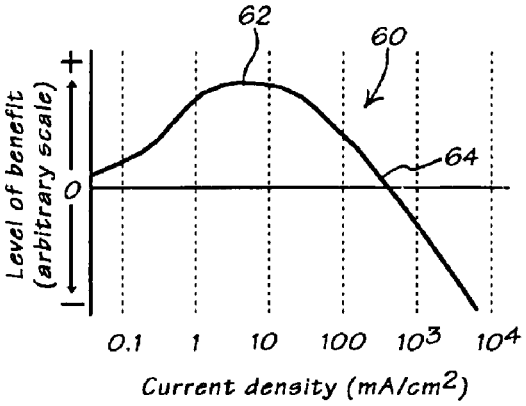
FIG. 3 is a schematic view of healing effect vs. signal intensity (amplitude)

A major point of difference between the waveforms of FIG. 4 and FIG. 1 is the inclusion of output interval $T_7$ (74g), during which intermediate voltage or current level $L_3$ ([76d] *76c*) is presented to the output or to the tissue being treated rather than low level $L_2$ (76b). The purpose of this change is to minimize the amount of low-frequency energy which is presented to the material being treated during this resting interval between pulse bursts.

Reference to line 38 in FIG. 1, for example, shows that a significant amount of charge remains on output capacitors or other filtering devices, and decays exponentially during interval 36 between pulse bursts. In FIG. 4, in contrast, interval $T_4$ (74d) defines a negative "equalizing" pulse at voltage or current level $L_2$ which substantially neutralizes any charge left on such devices. Once such neutralization has taken place, transition is made to level $L_3$ (76c) so that no significant output current flows during interval $T_7$ (74g), which makes up the remainder of the timing cycle.

Note that FIG. 4 shows no transition between interval $T_5$ and the first interval $T_1$ within any given interval $T_3$, since waveform 70 has level $L_1$ during both $T_1$ and $T_5$. Similarly, if $T_6$ approaches zero within a fraction of the normal transition time, there is no transition since waveform 70 has level $L_2$ during both interval $T_2$ and interval $T_4$.

Figure 5:
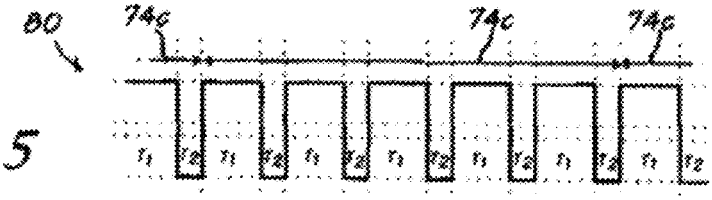
FIG. 5 illustrates an example of the waveform of FIG. 4.

A special case of the above-described waveform is that in which intervals $T_4$, $T_5$, $T_6$ and $T_7$ all approach zero, making the resulting waveform a continuous pulse train alternating between voltage or current levels $L_1$ and $L_2$ for intervals of $T_1$ and $T_2$ respectively, as shown in FIG. 5. In this case, $T_3$ (74c) of a waveform 80 may be considered to have any length which is an integral multiple of the sum of $T_1$ and $T_2$. While the pulse-burst waveform 70 is generally preferable, a continuous waveform 80 using the same values of $T_1$ and $T_2$ may prove more effective when the time available for treatment is limited.

For any waveform 70 or 80, one or more parameters such as the sum of intervals $T_1$ and $T_2$ or the span between voltage/current levels $L_1$ and $L_2$ may be varied for particular applications. For example, $L_1$ and $L_2$ may be adjusted, preferably together so that the ratio between them is preserved, to compensate for variable user skin impedance or to activate different tissue repair processes. Similarly, the span between voltages or currents $L_1$ and $L_2$ at the output of a treatment unit may be varied so as to compensate for variable tissue cross-sections under treatment or differing optimal current densities of various tissues.

Conditions presently believed to be treatable with a waveform such as 70 or 80 include, but are not necessarily limited to, the following: bone fractures, osteoporosis, acute pain, chronic pain, swelling, simple inflammation, and inflammatory disorders such as tendonitis (including carpal tunnel syndrome and other repetitive stress injuries) and osteoarthritis. However, it should be understood that no one set of timing intervals $T_1$-$T_7$ and voltage/current levels $L_1$-$L_3$ (or $L_1$-$L_4$) are useful for treating all (or even most) of these conditions. Accelerated healing of wounds, involving a variety of tissue types and resulting either from trauma or from degenerative conditions such as diabetes, may also be seen during treatment with waveforms 72, 80. While not wishing to be bound by theory, it is believed that appropriate voltage/current levels and timing intervals may be used to treat a wider variety of conditions whose etiology involves improper rates or imbalances in cell metabolism, secretion or replication, or which can be relieved by suitably modifying these factors. Thus, it should be understood that the optimum waveform characteristics for each particular application are best found with a modest combination of observation and experimentation.

A waveform according to the present invention, such as waveforms 70, 80, can be generated with an apparatus 90 shown in block diagram form in FIG. 6. Apparatus 90 includes a first timing block 92 which generates a succession of intervals $T_1$ and $T_2$, and optionally also $T_5$ and $T_6$; a second timing block 94 which generates a succession of intervals $T_3$ and optionally also $T_4$ and $T_7$; an interconnection block 96 which combines the signals from blocks 92 and 94 so that the succession of intervals $T_1$ and $T_2$ appears only during intervals $T_3$; a voltage or current switch 98 which generates an output signal at usable intensity; an optional adjustment block 100 for modifying the signal timing and intensity (i.e., amplitude); a filter 102 which removes unwanted signal components and preferably also sets transition and decay time constants; a connection block 104 which passes the signal out to a load 106 (cell culture, tissue, organism or part thereof, etc.); and a power supply 108 which provides energy as needed to enable the other components of apparatus 90 to perform their functions.

When present, adjustment block 100 may provide the capability of selecting from among a plurality of alternative, paired values of intervals $T_1$ and $T_2$, of intervals $T_4$ and $T_7$, or of both sets of intervals. More preferably, such paired interval values are selected so as to change the operating frequency of apparatus 90 while maintaining a selected duty cycle, or vice-versa. For example, one such paired value set of intervals $T_4$ and $T_7$ is one in which both members approach zero, thereby making the output a continuous pulse train such as waveform 80.

Optional adjustment block 100 may also provide the capability of selecting among a plurality of alternative values of voltage or current levels $L_1$, L2 and L3 in order to establish an optimal current density within the living matter being treated (i.e., load 106), as may be needed or desired for a specific application. To this end, switch 98 may generate an output waveform 70 or 80 as a voltage waveform, which is then converted to a current waveform by passage through a suitable resistor, resistor network or voltage-controlled current source making up a part of filter 102 under the control of adjustment block 100.

Filter 102 preferably includes one or more nonpolarized capacitors, or back-to-back combinations of electrolytic capacitors, connected in series with the output so as to block any direct-current component from the signal unless such a component is desired for a specific application. However, other types of devices may also be useful for filter 102.

Filter 102 preferably also includes suitable devices for blocking frequencies above a selected level (i.e., frequencies greater than the highest ones intentionally generated), to create a desired transition profile or to prevent interference by external high-frequency signal sources, as may be convenient. For example, filter 102 may include a shunt capacitance placed across the output lines after the signal has passed through the previously-mentioned resistor, resistor network or voltage-controlled current source so as simultaneously to slow and control the rate of transitions, to attenuate output frequency components above about 50 KHz, and to prevent interference with circuit functioning by any radio-frequency signals coming from the outside.

Filter 102 may also include any suitable type of rectifier for converting an otherwise biphasic output with no net DC content into a quasi-monophasic output with controlled DC content (as may be desirable for some wound-healing applications). If rectification is used, a switch may also be provided by which rectification may be turned on or off as may be needed for a specific case or phase of treatment. With rectification, it may be convenient to eliminate interval $T_7$, or to set output levels $L_2$ and $L_3$ relatively close together.

Blocks 92, 94, 96, 98, 100, 102, 104, 108 of FIG. 6 may be implemented in any of a wide variety of ways. For example, timing blocks 92 and 94 may both be astable multivibrators whose outputs are further processed by digital logic, constituting interconnection block 96, in approximately the manner which was described in U.S. Pat. No. 5,217,009 (incorporated herein by reference). Alternatively, timing block 92 may be an astable multivibrator with timing block 94 then derived from block 92 digitally, for example, by a frequency-divider chain. Timing blocks 92 and 94 may both be derived digitally from a common timing source, using a divider chain or microprocessor, in approximately the manner which was described in U.S. Pat. No. 5,413,596 (incorporated herein by reference). In yet another approach, both timing blocks 92 and 94 may be astable multivibrators, with block 94 controlling block 92 so that block 92 runs, generating intervals $T_1$ and $T_2$, only during interval $T_3$ and is turned off at other times, in approximately the manner which was described in U.S. Pat. No. 6,011,994 (incorporated herein by reference).

A timing block particularly well-suited for generating asymmetric, repeating waveforms such as 70 and 80 is based on complementary metal-oxide-semiconductor (CMOS) logic. It is a little-known fact that a CMOS logic gate can function as either an analog or a digital device, or as both at once. This permits many signal generation and processing operations to be performed in a surprisingly effective and straightforward manner using CMOS logic gates with analog or mixed signals as inputs. A self-starting, asymmetric CMOS oscillator 120 (technically, an astable multivibrator) based on this principle, consisting of two inverting logic gates 122a and 122b and a handful of passive components, was described in U.S. Pat. No. 6,011,994 and is shown in schematic form in FIG. 7. Oscillator 120 generates two complementary outputs 124a and 124b, each consisting of a succession of alternating intervals of high and low voltage, whose durations depend upon the values of capacitor 126 and resistors 128a, 128b and 128c, and the polarity of diode 130. Such an oscillator can function as either timing block 92 or timing block 94 in FIG. 6. Using the complementary outputs 124a and 124b in differential mode, rather than either of the outputs against a fixed potential, yields a peak-to-peak output voltage of nearly twice the supply voltage.

With a diode 130 connected as shown, and neglecting nonideal behavior of circuit components:

$$T_1=1.1R_1C,$$

$$T_2=1.1C/(1/R_1+1/R_2),$$

$$F=1/(T_1+T_2),$$

and $$D=T_1/(T_1+T_2)$$

where $T_1$ is the "high" output period of waveform 124a, $T_2$ its "low" output period, $R_1$ the value of resistor 128a, $R_2$ that of resistor 128b, C that of capacitor 126, F the oscillation frequency and D the duty cycle, provided that $R_3$, the value of resistor 128c, is large compared with $R_1$ and $R_2$. For waveform 124b, $T_1$ and $T_2$ are reversed. $T_1$ and $T_2$ are also reversed in both waveforms if the polarity of diode 130 is reversed.

Suitable values for these components may be found by first specifying a practical nonpolarized capacitor value typically in the range from about 100 pF to about 1 μF; calculating $R_1$ and $R_2$ from the equations $$R_1=T_1/(1.1\times C),$$

and $$R_2=1/(1.1\times C(1/T_1+1/T_2));$$

assigning $R_3$ any practical value at least twice and preferably approximately ten times $R_2$; then optimizing $R_1$ and $R_2$ (by a modest amount of experimentation) to compensate for the nonidealities of real-world components. Optimized values for $R_1$ and $R_2$ typically lie within approximately ±20-30% of those calculated as described above. In no case should $R_1$ or $R_2$ be less than about 3300 ohms nor more than about 3.3 MΩ, nor $R_3$ greater than about 22 MΩ. If this occurs, a new value should be chosen for C in order to bring $R_1$, $R_2$ and $R_3$ back within these ranges.

An oscillator 120 such as this can provide virtually any desired oscillation period from several seconds down to 1 μsec or less, and any desired duty cycle within such an oscillation. Particularly useful is the fact that the oscillation frequency can be changed without substantially altering the duty cycle, simply by changing the value of capacitor 126. This feature makes it possible to select among a plurality of alternative, paired values of $T_1$ and $T_2$ while preserving a desired duty cycle, for example, through the use of a switch selecting one of a plurality of capacitors.

Two such oscillators 120 can be interconnected so that one of them, oscillating at a relatively low frequency, controls the second, which oscillates at a much higher frequency but only during a selected phase of the lower-frequency oscillation (either $T_1$ or $T_2$), thereby generating a waveform similar to that shown in FIG. 1. Such an interconnected pair of oscillators 120a, 120b, shown in FIG. 8, can function as timing block 92 and 94 of FIG. 6, with the connection between the two oscillators serving simultaneously as interconnection block 96. An advantage of this approach is that, since the power consumption of a CMOS circuit (neglecting output loading) is strongly dependent on the operating frequency, turning off the higher-frequency oscillator except during that portion of the lower-frequency oscillation when it is needed minimizes the power consumption.

Two such coupled CMOS oscillators can also be used to generate the equalizing pulse of interval $T_4$. More preferably, the two complementary outputs of the higher-frequency oscillator are buffered and transformed by an added, mixed analog and digital stage so that they generate output voltage or current level $L_1$ when in one set of opposite logic states, another voltage or current level $L_2$ when in the opposite set, and a third level $L_3$ when, at the end of interval $T_4$, both outputs are brought to like logic states.

In a preferred embodiment, apparatus 90 generates a plurality of specific waveforms aimed at various biomedical applications, including but not necessarily limited to fracture healing, pain relief, and osteoporosis treatment. For example, a particular embodiment of apparatus 90 may generate the six waveforms illustrated in FIG. 9, in any of a plurality of user-selectable intensities. Here, waveforms 150, 152, and 154 are pulse-burst type waveforms, each having a different set of values for intervals $T_1$, $T_2$, $T_5$ and $T_6$; while $T_3$, $T_4$ and $T_7$ are the same in all three. Waveforms 156, 158 and 160 are continuous pulse-train equivalents of waveforms 150, 152, and 154, respectively, differing from them chiefly in that $T_4$ and $T_7$ are in each case are set to zero. An example of a set of timing intervals for the waveforms of FIG. 9 is given in Table 1.

TABLE 1

Figure 9:
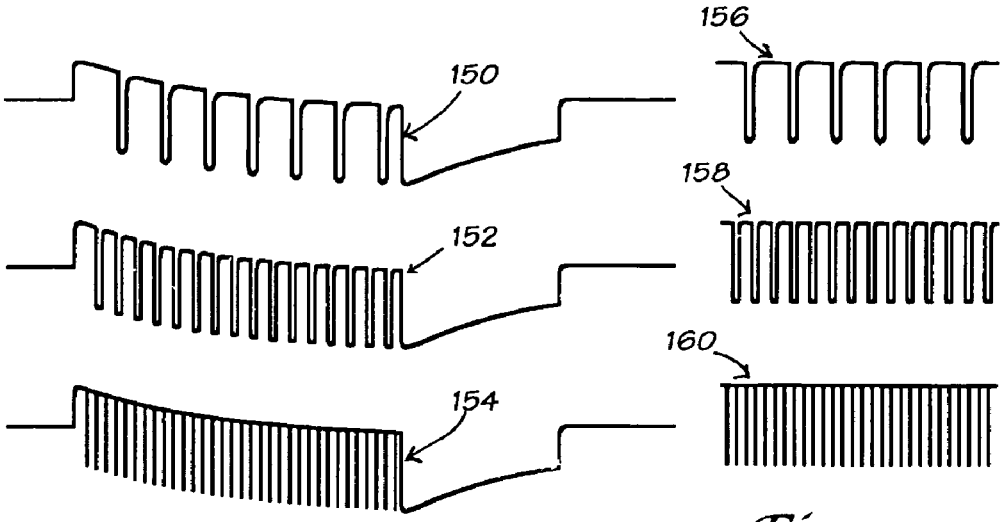
FIG. 9 shows a plurality of waveforms output by a particular embodiment of the apparatus of FIG. 6.

Timing intervals for waveforms 150, 152, 154, 156, 158, and 160 (FIG. 9).

| | Timing Interval* | | | | | | |
|---|---|---|---|---|---|---|---|
| Waveform | $T_1$ | $T_2$ | $T_3$ | $T_4$ | $T_5$ | $T_6$ | $T_7$ |
| 150 | 200 | 30 | 10 | 3 | 50 | — | 54 |
| 156 | 200 | 30 | — | 0 | 50 | — | 0 |
| 152 | 600 | 70 | 10 | 3 | 150 | — | 54 |
| 158 | 600 | 70 | — | 0 | 150 | — | 0 |
| 154 | 1500 | 170 | 10 | 3 | 400 | — | 54 |
| 160 | 1500 | 170 | — | 0 | 400 | — | 0 |

*($T_1$, $T_2$, $T_5$, and $T_6$ are given in μsec; $T_3$, $T_4$, and $T_7$ are in msec)

Timing accuracy for the example of Table 1 is about ±10% or 20 μsec, whichever is larger. An apparatus 90 with these timing intervals has been approved by the U.S. Food and Drug Administration for use in the relief of chronic pain.

When one CMOS oscillator of this type controls another in the manner shown, interval $T_5$ is the starting delay of the higher-frequency oscillator at the start of a pulse burst and is typically about one-fourth of interval $T_1$, while interval $T_6$ is simply that portion of the last interval $T_1$ which remains at the end of interval $T_3$. Hence, no attempt is made to define $T_6$ beyond what has already been given. Intervals $T_3$, $T_4$ and $T_7$ have the same values for all three pulse-burst waveforms, for the continuous waveforms, interval $T_3$ is undefined while $T_4$ and $T_7$ are both zero.

Intervals $T_1$ and $T_2$ are selected so that, for a pulse-burst type waveform, each burst may be divided either into approximately 6-8 pulses ("low modulation") as in waveform 150, approximately 15-32 pulses ("medium modulation") as in waveform 152, or approximately 35-72pulses ("high modulation") as in waveform 154. The same values of intervals $T_1$ and $T_2$ are used in the corresponding continuous pulse-train waveforms.

To compensate for variable tissue cross-sections to be treated or differing optimal current densities of various tissues, preset intensities for each waveform may be provided as shown in Table 2.

Table 2. Nominal output current (total output current from connection block 104 into load 106, measured according to ANSI/AAMI Standard No. NS-4-1985. Within load 106, the current is distributed approximately uniformly across the full cross-section of the load, with local variations depending on the particular tissue types present).

| | Output Current (μA) | |
|---|---|---|
| Setting | Pulse-Burst Mode | Continuous Mode |
| LOW | 60 | 180 |
| MEDIUM | 200 | 600 |
| HIGH | 600 | 1800 |

In general, pulse-burst operation is recommended for treatment periods of approximately one hour or more; treatment periods up to eight hours per day or even higher are recommended for many conditions. Where available treatment time is restricted to an hour or less, however, continuous pulse-train operation may be preferred. Low modulation is recommended for treating patients with thin or moist skin, medium modulation for normal skin, and high modulation for thick or dry skin. Similarly, low intensity is recommended for use on the fingers, medium intensity on the hands and arms, and high intensity elsewhere on the body. However, the optimum combination of settings is best determined individually for each particular patient being treated; a modicum of experimentation may be applied to find the most effective combination of settings in any particular case. As noted above, waveforms 150-160 meet all the safety requirements of ANSI/AAMI NS-4-1985. As a result, an apparatus 90 with the settings set forth in Tables 1 and 2 can safely be used wherever a conventional microcurrent electrostimulator or TENS unit can be used.

An apparatus 90 with the output parameters of Tables 1 and 2 includes parts corresponding to each of blocks 92-108 of FIG. 6, examples of which will be set forth below. While specific, preferred through-hole type parts numbers are sometimes given in the following descriptions, it should be understood that different components (including surface-mount type devices) and components manufactured according to differing technologies may also be useful. Resistors are typically ¼-watt, metal or metal-oxide film types with ±1% tolerance unless stated otherwise.

Figure 10:
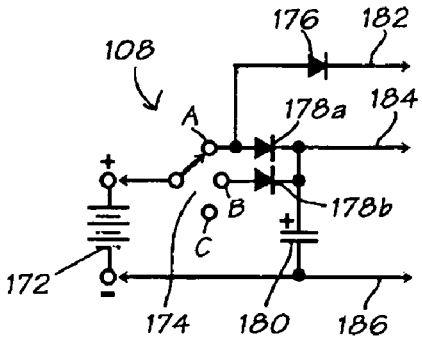
FIGS. 10, 11, and 12 show a power supply, a pair of timing blocks, and a voltage switching block and filter with associated circuitry, respectively, all being usable with the apparatus of FIG. 6.

Power supply 108, shown in FIG. 10, includes a replaceable battery 172; a three-position, on/off and function selector switch 174; a steering diode 176 for function selection; a pair of blocking diodes 178a and 178b to prevent damage should battery 174 be inserted backwards; and an electrolytic bypass capacitor 180 which provides a charge reservoir for circuit operation. No adapter, socket or other device for external power input is provided. In a preferred embodiment of the invention, the battery compartment for battery 172 is designed so that apparatus 90 operates only when the compartment is closed.

Battery 172 may have a nominal output of nine volts or thereabouts. Output voltages in this range may be provided by a series stack of three 3-volt lithium coin cells with capacities of at least approximately 270 milliampere-hours each, for example, Type 2032 lithium coin cells surrounded by a heat-shrunk sleeve trimmed flush with the most positive and most negative cell faces. Such a stack powers an apparatus 90 with the particular components described below for approximately two weeks of continuous use. For longer run times, larger coin cells may be used or a plurality of such cells may be connected in parallel. Lithium cells are preferred because of their combination of small size, long shelf life, high energy density, and relatively flat discharge curve under low and approximately constant loading; however, other types of batteries may also be useful.

In the embodiment shown in FIG. 10, position "A" of selector switch 174 disables control oscillator 190 via diode 176 and output line 182, selecting continuous pulse-train mode; position "B" allows both oscillators to run, generating pulse bursts, while position "C" is "off". Positions "C", "B" and "A" of switch 176 thus correspond to "OFF", "BURST" and "CONTINUOUS" operating modes, respectively.

Diodes 178a and 178b prevent accidental damage from reversed battery insertion in switch positions "A" and "B" respectively. Capacitor 180 provides an energy buffer to minimize the effects of rising internal resistance in battery 174 near the end of the battery's useful life. Output lines 184 and 186 from capacitor 180 are respectively +9 volts nominal and ground, supplying power to the remaining circuit blocks including connections, otherwise not shown, between these lines and the CMOS logic devices in these blocks.

Switch 174 may be an on-on-on type, single-pole 3-position (SP3T) miniature slide switch, such as an NKK type SS14SDP2. Diodes 176, 178a and 178b are small general-purpose silicon rectifiers, such as Diodes Incorporated type BAV19 or a similar type of rectifier. Capacitor 180 may be any common, miniature aluminum or tantalum:electrolytic type with a capacity of at least approximately 100 μF at 10 volts DC or higher.

Figure 8:
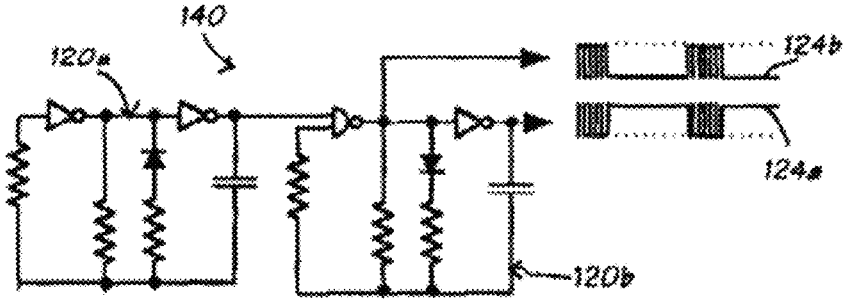
Figure 11:
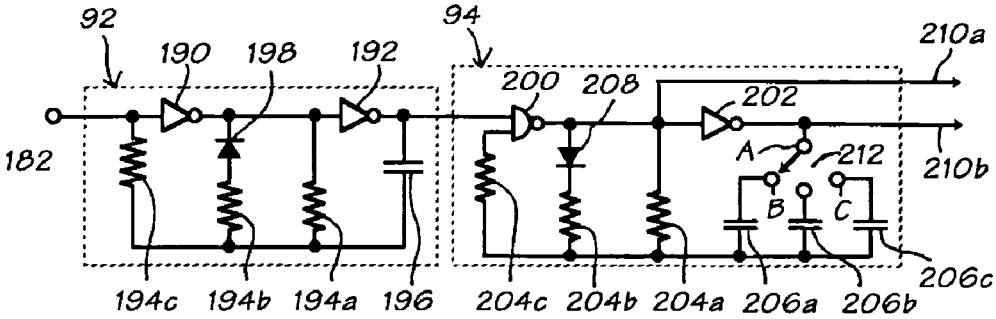

FIG. 11 shows timing blocks 92 and 94 in the same configuration previously shown in FIG. 8. First timing block 92 includes two CMOS logic gates 190 and 192; three resistors 194a, 194b and 194c; a capacitor 196; and a diode 198. These components form an astable, asymmetric multivibrator as shown in FIG. 6. Gates 190 and 192 may be two of the four 2-input NAND gates in a CD4011B quad package, connected with lines 184 and 186 as positive and negative supply, and preferably with each gate having one input tied "high" so that it functions as a simple inverter with minimal input and supply currents. Alternatively, an inverter may be formed by tying both gate inputs together.

In a typical implementation, resistors 194a, 194b and 194c may have values of 732 KΩ, 212 KΩ, and 2.2 MΩ, respectively, with tolerances of ±1%. However, these values may differ depending on factors such as the type of device, manufacturer, and lot number, but may be optimized as previously described. Capacitor 196 is a polypropylene or polyester film type capacitor with a value of approximately 0.100 μF at ±2% tolerance. Diode 198 is a small general-purpose silicon rectifier, preferably a BAV19 or similar type.

Similarly, second timing block 94 consists of two CMOS logic gates 200 and 202; three resistors 204a, 204b and 204c; three capacitors 206a, 206b and 206c, only one of which is selected at a time; and a diode 208. These form the same type of oscillator just described, except that this one accepts a control input and generates complementary outputs in the manner which was shown in FIG. 7. Gates 200 and 202 are preferably two of the four 2-input NAND gates in a CD4011B quad package, connected with lines 184 and 186 as positive and negative supply.

Gate 200 receives as one input the output of gate 192, so that oscillator 94 is turned on when this line is "high" and off when it is "low" (this connection corresponds to interconnection block 96 of FIG. 6). Since signal 192 has a low duty cycle, oscillator 94 runs only for a small fraction of the total time. Gate 202 has one input tied "high" in the same manner as gates 190 and 192. Gates 200 and 202 respectively feed output lines 210a and 210b with complementary pulse-burst signals in the manner which was explained with FIG. 8.

Selection among capacitors 206a, 206b and 206c is made through a three-position switch 212, which functions as a part of adjustment block 100 (FIG. 6). Capacitor 206a has the highest value of the three, and capacitor 206c the lowest. Hence, these three capacitors respectively provide the "LOW", "MEDIUM" and "HIGH" modulation settings.

Figure 7:
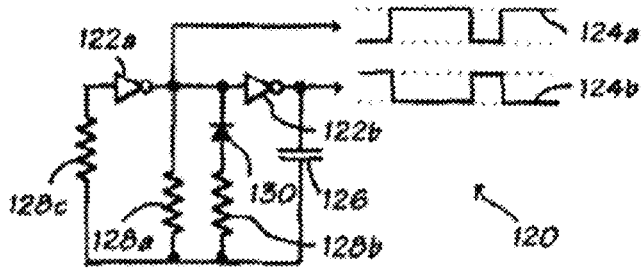
FIGS. 7 and 8 show an asymmetric oscillator circuit and a dual asymmetric oscillator circuit, respectively, both being usable with the apparatus of FIG. 6.

For purposes of illustration, diode 208 is shown in FIG. 11 with polarity opposite that of diode 198. This arrangement causes the generation of complementary outputs (as shown in FIG. 7) with a low duty cycle on line 210a and a correspondingly high duty cycle on line 210b. Alternatively, reversing diode 208 reverses this relationship while the outputs remain complementary.

In a typical implementation, resistors 204a, 204b and 204c may have values of 147 KΩ, 15.4 KΩ, and 2.2 MΩ respectively, with tolerances of ±1%. (The optimum values of any circuit components provided herein as examples may differ depending on the type of device, manufacturer, lot number, and so forth, and may be found by a modest amount of experimentation for each particular application.) Capacitors 206a, 206b and 206c are preferably polypropylene or polyester film types with ±2% tolerances and values of 0.0068 μF, 0.0027 μF and 0.001 μF, respectively. Diode 208 is a small general-purpose silicon rectifier, preferably a BAV19 or close functional equivalent.

Figure 12:
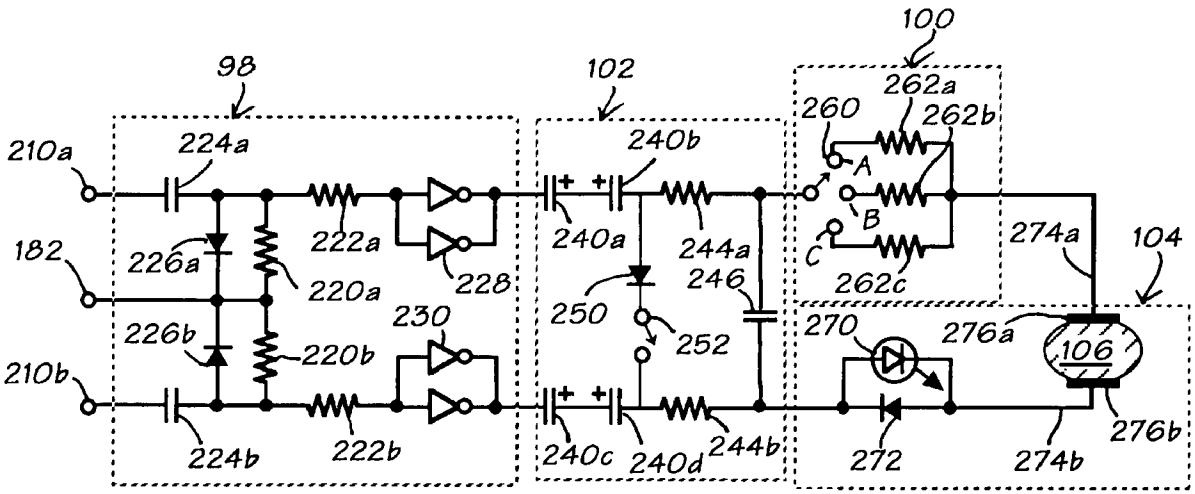

Voltage switching block 98, filter 102, an associated part of adjustment block 100, and connection block 104 are shown together in FIG. 12. Voltage switching block 98 consists of two pull-up resistors 220a and 220b, two input protection resistors 222a and 222b, two signal coupling capacitors 224a and 224b, two bypass diodes 226a and 226b, and two CMOS inverters 228 and 230. For added current-handling capacity, each of inverters 228 and 230 may be formed by two standard CMOS logic gates of matched switching characteristics connected with inputs and outputs in parallel, and powered in common by lines 184 and 186 as positive and negative supply, rather than by a single gate. More preferably, both inverters are formed from the four 2-input NAND gates in a single CD4011B quad package or similar devices taken in pairs.

Pull-up resistor 220a and coupling capacitor 224a together form a high-pass filter which transfers fast-changing signals from line 210a to the inputs of inverter 228 with minimal distortion, but draws these inputs to logic "high" when no fast-changing signals are present. Resistor 222a and diode 226a prevent voltage or current overshoots which might damage the inverter inputs. Resistors 220b and 222b, capacitor 224b and diode 226b serve an identical function with line 210b and inverter 230. As a result, the outputs of inverters 228 and 230 reproduce the complementary outputs of gates 202 and 200 respectively when oscillator 94 is running, but both assume equal logic "low" potentials if no transitions have taken place on these lines within a specified delay time. The differential voltage between these outputs then becomes zero, midway between its positive and negative peak values, corresponding to interval $T_7$ in FIG. 4.

Filter 102 is made up of capacitors 240a-240d, resistors 244a and 244b, and capacitor 246. Connected in series with the output of each inverter 228 and 230 is a pair of electrolytic capacitors 240a and 240b (or 240c and 240d) with their anodes tied together, thus forming a single, effectively nonpolarized capacitor which will pass a fast-changing signal but block any direct-current component. Nonpolarized electrolytic capacitors made for audiophile applications may also be useful; however, these types of capacitors may have excessive leakage current for use with the present invention.

Placed in series with each such capacitor pair is a resistor 244a or 244b, beyond which both lines are bridged by capacitor 246. The function of resistors 244a and 244b and capacitor 246 is to filter out unwanted high-frequency signal components of signals leaving the inverters, while simultaneously blocking the entry of outside high-frequency signals which might interfere with device functioning. The corner frequency of the resulting filter is preferably about 50 KHz.

After the end of a given pulse burst, capacitors 240a-240d discharge, as indicated by line 38 of FIG. 1 over interval 36, with a time constant which is set in part by the component values in filter 102 and the properties of load 106. When this curve reaches zero, capacitors 240a-240d hold no net charge.

Figure 13:
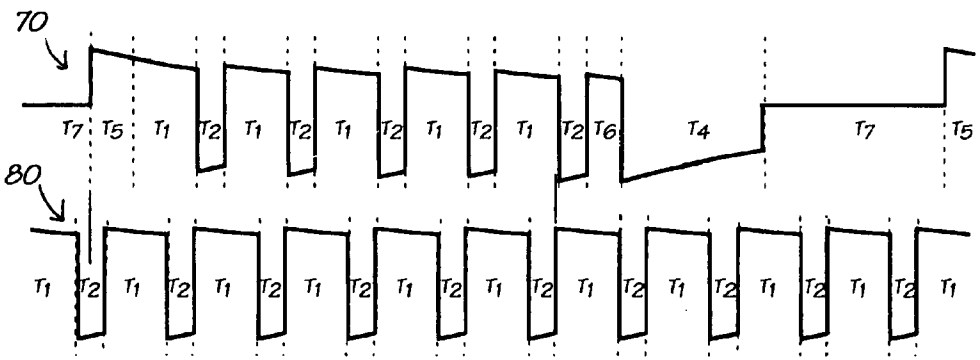
FIG. 13 is a schematic view of a pair of output waveforms.

At the end of the delay generated by resistors 220a and 222a, capacitor 224a and diode 226a, or by their "b" counterparts, the outputs of inverters 228 and 230 assume equal voltages, both logic "low". If this transition coincides with the passage of the capacitor discharge curve through voltage level $L_2$, the discharge curve is truncated at that point. Thereafter, since zero voltage is placed across the capacitors and zero charge remains on them, the output current is zero until the start of the next pulse burst. Such truncation is shown, for example, at the end of interval T4 in waveform 70 of FIG. 13.

While additional components may be needed to find the actual transition after each pulse burst, tests of the above-described apparatus 90 under typical loading conditions showed that after a 10-millisecond pulse burst, for example, the transition took place after about three more milliseconds. Since the curve is not particularly steep at this point, minor changes to component values in filter block 102 and to load 106 do not substantially affect the output. Hence, values for resistor 220a and capacitor 224a (and for 220b and 224b) may be found which give near-optimal performance over substantially all expected conditions of use. The resulting delay then becomes $T_4$ (74d in FIG. 4) while the following, substantially current-free "rest" period becomes $T_7$ (74g).

Resistors 220a and 222a, capacitor 224a and diode 226a (and their "b" counterparts) serve the additional safety function of forcing the outputs of inverters 228 and 230 both to logic "zero", and thus the output current to zero, in case of oscillator failure. This feature prevents electrolytic damage to tissue which might otherwise slowly occur if the oscillator failure took place in a device whose capacitors 222a through 222d had higher than nominal amounts of DC leakage. Values for resistors 220a and 220b, based on this criterion, are 681K each; for resistors 222a and 222b, 150K each; and for capacitors 224a and 224b, 0.0068 μF each. These capacitors are preferably miniature polypropylene or polyester types with ±2% tolerance. Capacitors 240a-240d are preferably small 10 μF aluminum or tantalum electrolytic types rated at 15 volts or higher, although each directly-connected pair may optionally be replaced with a single, nonpolarized capacitor of like value and voltage rating. Preferred practical values for resistors 244a and 244b are 332 ohms each. Diodes 226a and 226b are small general-purpose silicon rectifiers, preferably BAV19s or similar devices.

For some applications, such as stimulation of wound healing, it may be convenient to superimpose a controlled amount of DC upon waveform 70 rather than to suppress the DC content of the output, or to provide the ability to do so as an option. Preferably, the DC bias of the waveform is shifted without diminishing its amplitude. Diode 250 provides a simple rectification device by which this can be done, while switch 252 provides the flexibility of switching the diode into or out of the circuit as may be convenient.

In an alternative embodiment of the present invention, intended only for use with a DC-biased waveform 70, resistors 220a and 220b, and diodes 226a and 226b, are eliminated while capacitors 224a and 224b, switch 252, and, optionally, resistors 222a and 222b are replaced by short circuits. This renders both levels $L_2$ (76b) and $L_3$ (76c) substantially equal to zero, with level $L_1$ positive with respect to both $L_2$ and $L_3$ by approximately twice the supply voltage.

The magnitude of the output current delivered to load 106 is determined in part by switch 260, which functions as a part of adjustment block 100 by selecting any one of three different resistors 262a, 262b or 262c to be placed in series with capacitors 240a and 240b and resistor 244a. Resistor 262a has the highest value of the three, and resistor 262c the lowest. The selected resistor acts in concert with resistors 244a and 244b, the series combination of the three plus the internal resistance of inverters 228 and 230 serving to limit the output current to cell culture, tissue, organism or part thereof 106. Hence, these three resistors respectively provide the "LOW", "MEDIUM" and "HIGH" output intensity settings. Resistors 262a, 262b and 262c may have values of approximately 24.1 KΩ, 3.92 KΩ, and 332 Ω, respectively.

Output block 104 consists of diodes 270 and 272, wires 274a and 274b, and conductive block 276a and 276b by which physical contact is made with the living material 106 to be treated. At least one of diodes 270 and 272 is a light-emitting diode (LED), such as a Fairchild MV8412, while the other is a small silicon rectifier such as a BAV19. The LED may be either diode 270 as shown, or diode 272. However, for DC-biased (i.e., monophasic) operation, the LED is preferably that diode of 270, 272 which shares the polarity of diode 250 with respect to the output loop. Alternatively, both diodes may be LEDs. With the diodes arranged in antiparallel manner as shown (the anode of each tied to the cathode of the other) the pair is able to pass a high-frequency signal and emit light in proportion to the current flowing. This provides an indication simultaneously that the battery is providing adequate operating voltage, that all circuit blocks which it powers are functioning correctly, and that wires 274a and 274b and conductive block 276a and 276b are connected correctly to load 106.

Wires 274a and 274b are multistranded, fatigue-resistant wires, for example, 22 AWG equivalent wires with 30/37 stranding, insulated with a tough but flexible nonconductive material such as PVC. Their lengths may be chosen as needed for a specific application. Wires 274a and 274b, or sections thereof, may optionally be made removable from the remainder of the apparatus as shown, for example, by means of appropriate, FDA-acceptable plugs and sockets. Each of the wires may terminate in a 2 mm (0.080") diameter metal pin, miniature alligator clip or other device by which easy connection may be made to conductive blocks 276a and 276b.

Conductive blocks 276a and 276b may include electrically-conductive saline solutions or gels held in appropriate structures such as disposable or reusable electrode pads, salt bridges or other appropriate structures depending upon the intended use and type of load 106 to be treated. For example, saline gel electrodes may be adhered to the skin of a human or animal patient so that the field of current flow which is established between them includes the tissues to be treated. An example of such a gel electrode is the Uni-Patch "Multi-Day" #633; however, other types of electrodes may also be useful. Alternatively, block 276a and 276b may be in whole or in part of other materials, such as silver wire or silver-plated textile fabric, used in a similar fashion.

An apparatus 90, made using the component values given above and including all functions described, may be mounted in a small, lightweight housing of molded plastic or other suitable material, preferably a housing with a pocket clip or other means for convenient mounting to a bandage, cast, wrist or other band, or article of clothing. Most preferably, the housing is no larger than necessary to hold the described devices and the circuit board or boards which bear them. Suitable housings need be no larger than approximately 2.0"× 2.5"×0.75". Smaller housings may be useful if some or all of the described functions of apparatus 90 are implemented using surface-mount components, rather than the through-hole ones which have in some cases been identified in the descriptions above.

Apparatus 90 is lightweight, compact, self-contained, cost-effective to manufacture and maintain, and convenient to carry or wear for extended periods. It is safe for unsupervised home use without the need for special training, and able to generate the signals just described and deliver them efficiently through conductive pads making direct contact with the skin. Since only low voltages and currents are used, apparatus 90 does not pose a shock hazard even in case of malfunction. Power is furnished by compact and inexpensive batteries, needing replacement only once in several weeks of use.

An apparatus according to the invention is used to provide electrotherapeutic treatment for human and animal patients, including but not limited to healing acceleration, relief of acute or chronic pain, and relief of swelling and/or inflammation. However, the apparatus need not be confined to use with intact organisms, since isolated cells or tissue cultures can also be affected by electrotherapeutic waveforms (appropriate electrical stimuli have been observed to modify the rates of cell metabolism, secretion, and replication). Isolated skin cells, for example, might be treated with selected waveforms in an appropriate medium to increase cell proliferation and differentiation in the preparation of tissue-cultured, autogenous skin-graft material. As another example, the growth of bacteria genetically engineered to produce a desirable product, such as human insulin, might be accelerated, or their secretion of the desired product increased, by treatment with a suitable waveform.

With respect to the above description of the invention, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims.

What is claimed is:

1. An apparatus for generating an electrical signal for use in biomedical applications, said signal based on at least four timing intervals $T_1$-$T_4$, said apparatus comprising:

means for generating a set of at least four timing intervals $T_1$-$T_4$, said timing intervals having approximately the relationships (a) $(2\times T_2)\leqq T_1\leqq(20\times T_2)$.

(b) 50 μsec$\leqq(T_1+T_2)\leqq$5000 μsec, (c) $T_3\geqq(10\times T_1)$, and (d) $0\leqq T_4\leqq$500 msec; and means for combining said timing intervals into an electrical signal having an amplitude, *wherein said generating means is configured to produce a plurality of paired values of said intervals $T_1$ and $T_2$; and*

*means for selecting one of said paired values*.

2. The apparatus as recited in claim 1, further comprising means operably connected to said generating means for changing at least one of said intervals $T_1$ through $T_4$.

[3. The apparatus as recited in claim 1, wherein said generating means produces a plurality of paired values of said intervals $T_1$ and $T_2$, further comprising means for selecting one of said paired values.]

4. The apparatus as recited in claim 1, further comprising means for transmitting said electrical signal to a load.

5. [The apparatus as recited in claim 1] *An apparatus for generating an electrical signal for use in biomedical applications, said signal based on at least four timing intervals $T_1$-$T_4$, said apparatus comprising:*

*means for generating a set of at least four timing intervals $T_1$-$T_4$, said timing intervals having approximately the relationships*

*(a) $(2\times T_2)\leqq T_1\leqq(20\times T_2)$,*

*(b) 50 μsec$\leqq(T_1+T_2)\leqq$5000 μsec.*

*(c) $T_3\geqq(10\times T_1)$, and*

*(d) $0\leqq T_4\leqq$500 msec; and*

*means for combining said timing intervals into an electrical signal having an amplitude*, wherein said set of at least four timing intervals further comprises at least three additional timing intervals $T_5$-$T_7$, said at least three additional timing intervals having approximately the relationships (e) $0\leqq T_5\leqq T_1$, (f) $0\leqq T_6\leqq T_1$, (g) $0\leqq T_7\leqq$500 msec, and (f) 5 msec$\leqq(T_3+T_4+T_7)\leqq$500 msec.

6. The apparatus as recited in claim 5, wherein said interval $T_3$ further comprises a sequence containing an interval $T_5$, followed by at least one pair of intervals ($T_1$, $T_2$), followed by an interval $T_6$.

7. The apparatus as recited in claim 5, wherein said intervals $T_3$, $T_4$, and $T_7$ form a continuous sequence of repeating intervals $T_3$, $T_4$, $T_7$.

8. The apparatus as recited in claim 5, further comprising means operably connected to said generating means for changing at least one of said intervals $T_1$-$T_7$.

9. The apparatus as recited in claim 5, wherein said generating means produces a plurality of paired values of said intervals $T_4$ and $T_7$, further comprising means for selecting one of said paired values.

10. The apparatus as recited in claim 5, wherein said amplitude of said output signal further comprises:

a first level $L_1$ during said intervals $T_1$, $T_5$, and $T_6$;

a second level $L_2$ during said intervals $T_2$ and $T_4$; and a third level $L_3$ during said interval $T_7$, wherein $L_3$ is between $L_1$ and $L_2$.

11. The apparatus as recited in claim 10, wherein a transition between any two of said levels $L_1$ through $L_3$ has a decay time constant no greater than approximately one-half a length of said interval $T_2$.

12. The apparatus as recited in claim 10, further comprising a fourth level $L_4$, said level $L_4$ being intermediate said levels $L_1$ and $L_2$, wherein a transition between any of said levels $L_1$ through $L_3$ and said level $L_4$ has a decay time constant no less than approximately 10 times a length of said interval $T_1$.

13. The apparatus as recited in claim 10, further comprising means operably connected to said combining means for changing at least one of said levels $L_1$ through $L_3$.

14. The apparatus as recited in claim 10, further comprising means operably connected to said combining means for selecting among a plurality of values for said levels $L_1$ through $L_3$.

15. An apparatus for generating an electrical signal for use in biomedical applications, said signal based on at least four timing intervals $T_1$-$T_4$, said apparatus comprising:

a first timing block for generating a first timing interval $T_1$ and a second timing interval $T_2$;

a second timing block for generating a third timing interval $T_3$ and a fourth timing interval $T_4$, said intervals $T_1$-$T_4$ having approximately the relationships (a) $(2\times T_2)\leqq T_1\leqq(20\times T_2)$, (b) 50 μsec$\leqq(T_1+T_2)\leqq$5000 μsec, (c) $T_3\geqq(10\times T_1)$, and (d) $0\leqq T_4\leqq$500 msec; and an interconnection block operably connected between said first and second timing blocks, said interconnection block combining said intervals $T_1$-$T_4$; and means operably connected to said interconnection block for generating an output signal with said intervals $T_1$-$T_4$, said output signal having an amplitude.

16. The apparatus as recited in claim 15, further comprising a filter operably connected to said generating means, said filter transmitting signal components within a selected frequency range.

17. The apparatus as recited in claim 15, further comprising power supply means operably connected to said first and second timing blocks, said interconnection block, and said signal-generating means.

18. The apparatus as recited in claim 15, further comprising means operably connected to said generating means for changing said amplitude.

19. The apparatus as recited in claim 15, wherein said first and second timing blocks further comprise first and second astable multivibrators, respectively.

20. The apparatus as recited in claim 19, wherein said interconnection block uses an output of said first astable multivibrator to control said second astable multivibrator.

21. The apparatus as recited in claim 15, wherein said set of at least four timing intervals further comprises at least three additional timing intervals $T_5$-$T_7$, wherein said first timing block further comprises means for generating said intervals $T_5$ and $T_6$, wherein said second timing block further comprises means for generating said interval $T_7$, and wherein said at least four additional timing intervals have approximately the relationships (e) $0 \leqq T_5 \leqq T_1$, (f) $0 \leqq T_6 \leqq T_1$, (g) $0 \leqq T_7 \leqq 500$ msec, and (f) 5 msec$\leqq(T_3+T_4+T_7)\leqq$500 msec.

22. The apparatus as recited in claim 21, wherein said interval $T_3$ further comprises a sequence containing an interval $T_5$, followed by at least one pair of intervals ($T_1$, $T_2$), followed by an interval $T_6$.

23. The apparatus as recited in claim 21, wherein said interconnection block divides said interval $T_3$ into a sequence of shorter intervals, said sequence consisting of at least one interval $T_5$, followed by at least one pair of intervals ($T_1$, $T_2$), followed by at least one interval $T_6$.

24. The apparatus as recited in claim 21, further comprising means operably connected to said generating means for changing at least one of said intervals $T_1$-$T_7$.

25. The apparatus as recited in claim 21, wherein said generating means produces a plurality of paired values of said intervals $T_4$ and $T_7$, further comprising means for selecting one of said paired values.

26. The apparatus as recited in claim 21, wherein said amplitude of said output signal further comprises:

a first level $L_1$ during said intervals $T_1$, $T_5$, and $T_6$;

a second level $L_2$ during said intervals $T_2$ and $T_4$;

and a third level $L_3$ during said interval $T_7$, wherein $L_3$ is between $L_1$ and $L_2$; and means operably connected to said combining means for changing at least one of said levels $L_1$ through $L_3$.

27. The apparatus as recited in claim 26, wherein a transition between any two of said levels $L_1$ through $L_3$ has a decay time constant no greater than approximately one-sixth a length of said interval $T_2$.

28. The apparatus as recited in claim 26, further comprising a fourth level $L_4$, said level $L_4$ being intermediate said levels $L_1$ and $L_2$, an output voltage initially set at a selected one of said levels $L_1$ and $L_2$ decaying towards said level $L_4$ with a time constant no less than approximately 10 times a length of said interval $T_1$;

means operably connected to said combining means for changing said level $L_4$.

29. The apparatus as recited in claim 26, further comprising means operably connected to said combining means for selecting among a plurality of values for said levels $L_1$ through $L_3$.

30. A method for generating an electrical signal for use in biomedical applications, said method comprising:

generating at least four timing intervals $T_1$-$T_4$ having approximately the relationships (a) $(2\times T_2)\leqq T_1\leqq(20\times T_2)$, (b) 50 μsec$\leqq(T_1+T_2)\leqq$5000 μsec, (c) $T_3\geqq(10\times T_1)$, and (d) $0\leqq T_4\leqq$500 msec; [and]

combining said timing intervals into an electrical signal having an amplitude*; and*

*selecting one of a plurality of paired values of said intervals $T_1$ and $T_2$.*

[31. The method as recited in claim 30, further comprising selecting one of a plurality of paired values of said intervals $T_1$ and $T_2$.]

32. [The method as recited in claim 30, further comprising the step of] *A method for generating an electrical signal for use in biomedical applications, said method comprising:*

*generating at least four timing intervals $T_1$-$T_4$ having approximately the relationships:*

*(a) $(2+T_2)\leqq T_1(20+T_2)$,*

*(b) 50 μsec$\leqq(T_1+T_2)\leqq$5000 μsec,*

*(c) $T_3\geqq(10+T_1)$, and*

*(d) $0\leqq T_4\leqq$500 msec;*

*combining said timing intervals into an electrical signal having an amplitude;* generating at least three additional timing intervals having approximately the relationships (e) $0\leqq T5_4\leqq T_1$, (f) $0\leqq T_6\leqq T_1$, (g) $0\leqq T_7\leqq 500$ msec, and (f) 5 msec$\leqq(T_3+T_4+T_7)\leqq$500 msec; and combining said additional timing intervals with said intervals $T_1$-$T_4$ to produce said electrical signal.

33. The [apparatus] *method* as recited in claim 32, further comprising selecting one of a plurality of paired values of said intervals $T_4$ and $T_7$.

34. The method as recited in claim 32, further comprising:

adjusting said amplitude to a first level $L_1$ during said intervals $T_1$, $T_6$, and $T_7$;

adjusting said amplitude to a second level $L_2$ during said intervals $T_2$ and $T_4$; and adjusting said amplitude to a third level $L_3$ during said interval $T_7$, wherein $L_3$ is between $L_1$ and $L_2$.

35. The apparatus as recited in claim 34, further comprising means operably connected to said combining means for selecting among a plurality of values for said levels $L_1$ through $L_3$.

*36. A method comprising:*

*placing at least one electrically conductive body in contact with skin of a human or animal and applying a waveform of voltage or current to the electrically conductive body,*

*wherein the waveform comprises a first interval wherein the waveform is held substantially at zero polarity interspersed with a second interval wherein the waveform comprises a burst of pulses, the burst of pulses alternating between opposite polarities, the waveform at each polarity having a given duration that produces a substantially flat-topped waveform, the first interval being longer than the second interval, and wherein the duration of a first polarity of the opposite polarities comprises at least twice but not more than twenty times the duration of the opposite polarity.*

*37. The method of claim 36,*

*wherein each pulse of the second interval comprises a substantially rectangular waveform.*

*38. The method of claim 36, wherein the polarities are equal in magnitude.*

*39. The method of claim 36, wherein the polarities are non-equal in magnitude.*

*40. The method of claim 36, wherein the skin contact is through gel.*

*41. The method of claim 36, wherein the waveform is for electrotherapeutic treatment of the human or animal.*

*42. The method of claim 41, wherein the electrotherapeutic treatment is selected from the group consisting of stimulating fracture healing, stimulating wound healing, relieving acute pain, relieving chronic pain, treating osteoporosis, stimulating healing acceleration, relieving swelling, relieving inflammation, treating tendonitis, treating repetitive stress injuries, treating carpal tunnel syndrome, treating osteoarthritis, modifying the rate of cell metabolism, modifying cell secre-*

*tion, modifying cell replication, modifying cell proliferation and modifying cell differentiation.*

*43. The method of claim 36, wherein the waveform is*

*produced from a battery-operated, portable device suitable to be worn by a human or animal, and*

*applied to the human or animal with at least two electrically conductive bodies in contact with the skin of the human or animal.*

*44. The method of claim 36, wherein the method further comprises removing or minimizing unwanted components of the waveform through means selected from the group consisting of DC-blocking capacitors, an equalizing pulse to remove or minimize a DC component, and filtering means to remove or minimize unwanted AC frequencies.*

*45. The method of claim 44, wherein the waveform is applied for electrotherapeutic treatment to the human or animal.*

*46. The method of claim 45, wherein the electrotherapeutic treatment is selected from the group consisting of stimulating fracture healing, stimulating wound healing, relieving acute pain, relieving chronic pain, treating osteoporosis, stimulating healing acceleration, relieving swelling, relieving inflammation, treating tendonitis, treating repetitive stress injuries, treating carpal tunnel syndrome, treating osteoarthritis, modifying the rate of cell metabolism, modifying cell secretion, modifying cell replication, modifying cell proliferation and modifying cell differentiation.*

*47. The method of claim 44, wherein the waveform is*

*produced from a battery-operated, portable device suitable to be worn by a human or animal, and*

*applied to the human or animal with at least two electrically conductive bodies in contact with skin of the human or animal.*

*48. The method of claim 36, wherein the electrically conductive body is selected from the group consisting of an electrode and gel.*

*49. A method comprising:*

*applying a waveform to a human or animal,*

*wherein the waveform comprises a first interval wherein the waveform undergoes no transition interspersed with a second interval wherein the waveform includes a burst of pulses,*

*the first interval being longer than the second interval,*

*the waveform including an equalizing pulse at the end of a cycle to remove a DC component.*

*50. The method of claim 49,*

*wherein each pulse of the second interval comprises a substantially rectangular waveform.*

*51. The method of claim 49, wherein the burst of pulses alternates between two polarities.*

*52. The method of claim 51, wherein the polarities are opposite.*

*53. The method of claim 51, wherein the polarities are equal in magnitude.*

*54. The method of claim 51, wherein the polarities are non-equal in magnitude.*

*55. The method of claim 51, wherein one polarity is zero in magnitude.*

*56. The method of claim 51, wherein the duration of a first polarity of the opposite polarities comprises at least twice but not more than twenty times the duration of the opposite polarity.*

*57. The method of claim 49, wherein the waveform is applied to skin of the human or animal.*

*58. The method of claim 49, wherein the waveform is applied to human or animal skin for electrotherapeutic treatment of the human or animal.*

*59. The method of claim 58, wherein the skin contact is through gel.*

*60. The method of claim 58, wherein the electrotherapeutic treatment is selected from the group consisting of stimulating fracture healing, stimulating wound healing, relieving acute pain, relieving chronic pain, treating osteoporosis, stimulating healing acceleration, relieving swelling, relieving inflammation, treating tendonitis, treating repetitive stress injuries, treating carpal tunnel syndrome, treating osteoarthritis, modifying the rate of cell metabolism, modifying cell secretion, modifying cell replication, modifying cell proliferation and modifying cell differentiation.*

*61. A method comprising:*

*placing at least one electrically conductive body in contact with a medium containing isolated cells or cultured tissue and applying a waveform of voltage or current to the electrically conductive body,*

*wherein the waveform comprises a first interval wherein the waveform is held substantially at zero polarity interspersed with a second interval wherein the waveform comprises a burst of pulses, the burst of pulses alternating between opposite polarities, the waveform at each polarity having a given duration that produces a substantially flat-topped waveform, the first interval being longer than the second interval.*

*62. The method of claim 61,*

*wherein each pulse of the second interval comprises a substantially rectangular waveform.*

*63. The method of claim 61, wherein the duration of a first polarity of the opposite polarities comprises at least twice but not more than twenty times the duration of the opposite polarity.*

*64. The method of claim 61, wherein the polarities are equal in magnitude.*

*65. The method of claim 61, wherein the polarities are non-equal in magnitude.*

*66. The method of claim 61, wherein the waveform is applied to isolated cells or cultured tissue for electrostimulation of the isolated cells or cultured tissue.*

*67. The method of claim 66, wherein the electrostimulation results in an effect selected from the group consisting of modifying the rate of cell metabolism, modifying cell secretion, modifying cell replication, modifying cell proliferation and modifying cell differentiation.*

*68. The method of claim 67, wherein the method further comprises removing or minimizing unwanted components of the waveform through means selected from the group consisting of DC-blocking capacitors, an equalizing pulse to remove or minimize a DC component, and filtering means to remove or minimize unwanted AC frequencies.*

*69. The method of claim 61, wherein the waveform is*

*produced from a battery-operated, portable device,*

*and applied to the isolated cells or cultured tissue with at least two electrically conductive bodies.*

*70. The method of claim 69, wherein the waveform is applied to isolated cells or cultured tissue for electrostimulation of the isolated cells or cultured tissue.*

*71. The method of claim 70, wherein the electrostimulation results in the effect selected from the group consisting of modifying the rate of cell metabolism, modifying cell secretion, modifying cell replication, modifying cell proliferation and modifying cell differentiation.*

*72. The method of claim 61, wherein the electrically conductive body is selected from the group consisting of an electrode and gel.*

*73. An apparatus comprising:*

*a means for placing at least one electrically conductive body in contact with skin of a human or animal and applying a waveform of voltage or current to the electrically conductive body,*

*wherein the waveform comprises a first interval wherein the waveform is held substantially at zero polarity interspersed with a second interval wherein the waveform comprises a burst of pulses, the burst of pulses alternating between opposite polarities, the waveform at each polarity having a given duration that produces a substantially flat-topped waveform, the first interval being longer than the second interval, wherein the duration of a first polarity of the opposite polarities comprises at least twice but not more than twenty times the duration of the opposite polarity.*

*74. The apparatus of claim 73,*

*wherein each pulse of the second interval comprises a substantially rectangular waveform.*

*75. The apparatus of claim 73, wherein the waveform is applied to human or animal skin for electrotherapeutic treatment.*

*76. The apparatus of claim 75, wherein the electrotherapeutic treatment is selected from the group consisting of stimulating fracture healing, stimulating wound healing, relieving acute pain, relieving chronic pain, treating osteoporosis, stimulating healing acceleration, relieving swelling, relieving inflammation, treating tendonitis, treating repetitive stress injuries, treating carpal tunnel syndrome, treating osteoarthritis, modifying the rate of cell metabolism, modifying cell secretion, modifying cell replication, modifying cell proliferation and modifying cell differentiation.*

*77. The apparatus of claim 73, wherein the waveform is*

*produced from a battery-operated, portable device suitable to be worn by a human or animal, and*

*applied to the human or animal with at least two electrically conductive bodies in contact with the skin of the human or animal.*

*78. The apparatus of claim 73, wherein the apparatus further comprises removing or minimizing unwanted components of the waveform through means selected from the group consisting of DC-blocking capacitors, an equalizing pulse to remove or minimize a DC component, and filtering means to remove or minimize unwanted AC frequencies.*

* * * * *

UNITED STATES PATENT AND TRADEMARK OFFICE

CERTIFICATE OF CORRECTION

PATENT NO. : RE43,374 E
APPLICATION NO. : 11/084870
DATED : May 8, 2012
INVENTOR(S) : James W. Kronberg It is certified that error appears in the above-identified patent and that said Letters Patent is hereby corrected as shown below:

Column 21, Line 22:

" (a) $(2\times T_2)\leqq T_1\leqq(20\times T_2)$." should read -- (a) $(2\times T_2)\leqq T_1\leqq(20\times T_2)$, --.

Column 21, Line 48:

" (b) 50 $\mu$sec$\leqq(T_1+T_2)\leqq$5000 $\mu$sec." should read -- (b) 50 $\mu$sec$\leqq(T_1+T_2)\leqq$5000 $\mu$sec, --.

Column 24, Line 6:

" (a) $(2+T_2)\leqq T_1\leqq(20+T_2)$," should read -- (a) $(2\times T_2)\leqq T_1\leqq(20\times T_2)$, --.

Column 24, Line 8:

" (c) $T_3\geqq(10+T_1)$, *and* " should read -- (c) $T_3\geqq(10\times T_1)$, *and* --.

Signed and Sealed this
Twenty-sixth Day of February, 2013

Teresa Stanek Rea
*Acting Director of the United States Patent and Trademark Office*